United States Patent
Matherly et al.

(10) Patent No.: US 9,297,252 B2
(45) Date of Patent: Mar. 29, 2016

(54) USE OF LONG CHAIN AMINES AND DIFUNCTIONAL COMPOUNDS AS TRACERS

(71) Applicant: Baker Hughes Incorporated, Houston, TX (US)

(72) Inventors: Ronald M. Matherly, Sugar Land, TX (US); Grahame N. Taylor, Tomball, TX (US)

(73) Assignee: BAKER HUGHES INCORPORATED, Houston, TX (US)

( * ) Notice: Subject to any disclaimer, the term of this patent is extended or adjusted under 35 U.S.C. 154(b) by 0 days.

(21) Appl. No.: 14/567,332

(22) Filed: Dec. 11, 2014

(65) Prior Publication Data

US 2015/0377010 A1    Dec. 31, 2015

Related U.S. Application Data (63) Continuation-in-part of application No. 14/501,722, filed on Sep. 30, 2014, and a continuation-in-part of application No. 14/317,922, filed on Jun. 27, 2014.

(51) Int. Cl.
*E21B 47/10* (2012.01)
*C09K 8/86* (2006.01)

(52) U.S. Cl.
CPC .............. *E21B 47/1015* (2013.01); *C09K 8/86* (2013.01)

(58) Field of Classification Search
CPC ....... E21B 43/267; E21B 43/26; E21B 49/08; E21B 44/00
USPC ................. 166/250.12, 250.1, 250.01, 252.6, 166/308.1, 280.1, 280.2
See application file for complete search history.

(56) References Cited

U.S. PATENT DOCUMENTS 3,856,468 A * 12/1974 Keller .............................. 436/27
4,058,366 A * 11/1977 Cabbiness ....................... 436/27

(Continued)

FOREIGN PATENT DOCUMENTS

WO    2012069942 A1    5/2012

OTHER PUBLICATIONS

Galdiga, Claus Ulrich et al., "Ultra-trace determination of fluorinated aromatic carboxylic acids in aqueous reservoir fluids using solid-phase extraction in combination with gas chromatography-mass spectrometry," Jnl of Chromatography A., 793, pp. 297-306 (1998).

(Continued)

*Primary Examiner* — Zakiya W Bates
*Assistant Examiner* — Silvana Runyan
(74) *Attorney, Agent, or Firm* — Mossman Kumar & Tyler PC (57) ABSTRACT

Non-halogenated molecules including, but are not necessarily limited to, alkyl and aromatic amines having from 8 to 18 carbon atoms and salts of these amines, diols having the formula HO—$(CH_2)_n$—OH, diamines having the formula $H_2N$—$(CH_2)_n$—$NH_2$, dicarboxylic acids having the formula HO.CO—$(CH_2)_n$—CO.OH, diesters having the formula R'O.CO—$(CH_2)_n$—CO.OR", where n is 4 to 18, and R' and R" are independently straight or branched alkyl or aromatic groups of 1-20 carbon atoms, and combinations thereof are used as tracers to measure oil and/or water fluid returns, e.g. from a hydraulic fracturing job. The non-halogenated molecules may be combined with substrates and introduced into a subterranean location, desorbed and recovered from the subterranean location with a fluid, reacted with a reagent to give a derivatized tracer. The presence of the derivatized tracer is then detected in the recovered fluid. Different non-halogenated tracers may be used for each hydraulic fracturing stage.

19 Claims, 4 Drawing Sheets

(56) References Cited

U.S. PATENT DOCUMENTS

| | | | |
|---|---|---|---|
| 4,501,324 A | 2/1985 | Sandiford et al. | |
| 4,520,109 A | 5/1985 | Simmonds et al. | |
| 5,164,099 A | 11/1992 | Gupta et al. | |
| 5,256,572 A | 10/1993 | Tang et al. | |
| 6,126,872 A | 10/2000 | Kommareddi et al. | |
| 6,160,036 A | 12/2000 | Kommareddi et al. | |
| 6,645,769 B2 | 11/2003 | Tayebi et al. | |
| 6,841,593 B2 | 1/2005 | Kommareddi et al. | |
| 7,032,662 B2 | 4/2006 | Malone et al. | |
| 7,491,682 B2 | 2/2009 | Gupta et al. | |
| 7,493,955 B2 | 2/2009 | Gupta et al. | |
| 8,242,062 B2 | 8/2012 | Spall et al. | |
| 2004/0094297 A1* | 5/2004 | Malone et al. | 166/250.12 |
| 2006/0144588 A1 | 7/2006 | Ferguson et al. | |
| 2009/0025470 A1 | 1/2009 | Green et al. | |
| 2010/0307745 A1 | 12/2010 | Lafitte et al. | |
| 2011/0146974 A1* | 6/2011 | Hartshorne et al. | 166/250.12 |
| 2012/0165487 A1 | 6/2012 | Hoshino | |
| 2013/0087329 A1 | 4/2013 | Hewitt et al. | |
| 2013/0126158 A1* | 5/2013 | Gupta et al. | 166/250.12 |

OTHER PUBLICATIONS

Serres-Piole, Coralie et al., "New Passive Water Tracers for Oil Field Applications," Energy Fuels 25, pp. 4488-4496 (2011).

* cited by examiner

USE OF LONG CHAIN AMINES AND DIFUNCTIONAL COMPOUNDS AS TRACERS

CROSS-REFERENCES TO RELATED APPLICATIONS

This application is a continuation-in-part application of U.S. patent application Ser. No. 14/501,722 filed Sep. 30, 2014, and is a continuation-in-part application of U.S. patent application Ser. No. 14/317,922 filed Jun. 27, 2014, both of which are incorporated herein by reference in their entireties.

TECHNICAL FIELD

The present invention relates to methods and compositions for determining from which fracturing stage a particular fluid is produced in a multi-stage hydraulic fracturing operation, and more particularly relates to methods and compositions for determining from which fracturing stage a particular fluid is produced in a multi-stage hydraulic fracturing operation which does not use halogenated tracers.

TECHNICAL BACKGROUND

It is well known that hydrocarbons (oil and gas) are produced from wells drilled in the earth, hereinafter referred to as "oil wells." It is additionally well known that drilling a hole into the earth to reach oil and gas bearing formations is an expensive operation which limits the number of wells that can be economically drilled. It follows then that it is desirable to maximize both the overall recovery of hydrocarbons held in the formation and the rate of flow from the subsurface formation to the surface, where it can be recovered.

One way in which to maximize production is the process known as hydraulic fracturing. Hydraulic fracturing involves cracking or fracturing a portion of the hydrocarbon-bearing formation surrounding an oil well by injecting a specialized fluid into the wellbore directed at the face of the geologic formation at pressures sufficient to initiate and/or extend a fracture in the formation. Ideally, what this process creates is not a single fracture, but a fracture zone, that is, a complex zone having multiple fractures, or cracks in the formation, through which hydrocarbon can more readily flow to the wellbore. Proppants and other materials are pumped into the fractures or cracks to keep the fracture open once the hydraulic pressure is released. Such propped fractures have increased permeability compared to the surrounding rock, which improved permeability facilitates the production of hydrocarbons. The proppants or other materials may contain substrate particles such as diatomaceous earth (DE) that may have treating materials adsorbed or otherwise contained on the substrate. These treating materials may include, but are not necessarily limited to, scale inhibitors, paraffin inhibitors, corrosion inhibitors, and the like, which may desorb from the substrate particles to treat the produced hydrocarbons.

Fracturing fluids can vary widely in composition. Slick water is water to which has been added chemicals to increase its fluid flow, notably friction reducers such as a polyacrylamide. Friction reducers improve the ability of the fluid to be pumped under pressure to cause fracturing and with less power than essentially only water. Other optional components include biocides, corrosion inhibitors, scale inhibitors and the like. Fracturing fluids may also comprise water that has been viscosified, such as by using a crosslinked or non-crosslinked polysaccharide such as guar gum or the like, and/or by using a viscoelastic surfactant (VES) such as an amidoamine oxide.

Creating a fracture in a hydrocarbon-bearing formation requires several materials. Often these materials, if not removed from the oil well, can subsequently interfere with oil and gas production. Even the drilling mud used to lubricate a drill bit during the drilling of an oil well can interfere with oil and gas production. Taking too long to remove such materials can increase the cost to the operator of the well by delaying production and causing excess removal expenses. Not being thorough in removing such materials can increase the cost to the operator of the well through lower production rates and possible lost production.

Measures taken to remove unwanted or unneeded materials are usually inexact. Sometimes additional fluids are used to flush out unwanted materials in the well bore. In other situations, reservoir fluids flow can make estimating return flow very difficult, particularly if the reservoir fluids are incompatible with the injected materials. It would be desirable in the art of oil and gas production to be able to determine how much of a given material is left in an oil well after a drilling, fracturing or any other operation requiring the injection of materials into an oil well. Tracers included in the material are a known way of determining the presence, and sometimes the amount, of a given material remaining in or retrieved from an oil well with which the tracers are associated.

One hydraulic fracturing technique uses multiple fracturing stages where different isolated zones are fractured in different ways designed or customized for each zone. However, once the well is placed into production, and the fluids from all zones are produced together, it generally cannot be determined from which zone a particular portion of the fluid was produced since the fluids are intermingled. In the past, unique halogenated tracers have been injected into each of the respective zones, and by means of distinguishing the produced tracers and their associated fluids, it may be determined what types of fluids (and their compositions) are produced from which zones. Further, the tracers may help maximize the production of oil and gas. If it is determined that water is overwhelmingly produced from one particular zone, that zone could be isolated and shut off from production so that less overall water is produced and the hydrocarbon production may be maximized.

In the past, perfluorinated compounds have been used as tracers to measure oil returns from a fracturing job. These compounds have a one particular key advantage and many disadvantages. Their main advantage is they are easy to detect. However, they are very expensive, and further, separating one compound from another is very difficult. Also, halogenated compounds remaining in the produced fluids will poison the catalyst in the downstream refineries.

It would be particularly desirable if these goals could be achieved using inexpensive tracers which are easily distinguished from one another.

SUMMARY

There is provided, in one non-limiting form, a method for determining the presence of a tracer from a subterranean location, which method includes introducing at least one non-halogenated tracer into a subterranean location, where the at least one non-halogenated tracer is selected from the group consisting of primary or secondary alkyl and aromatic amines with the formula $H_2N-R$ or $R'-HN-R''$ having from 8 to 18 carbon atoms and salts of these amines, alkyl or aromatic diols having the formula $HO-(CH_2)_n-OH$, diamines having the formula $H_2N-(CH_2)_n-NH_2$, dicarboxylic acids having the formula $HO.CO-(CH_2)_n-CO.OH$, diesters having the formula $R'O.CO-(CH_2)_n-$ CO.OR", where n is 4 to 18, and R' and R" are independently straight or branched alkyl or aromatic groups of 1-20 carbon atoms, and combinations thereof, where the non-halogenated tracer is absorbed into and/or adsorbed onto a plurality of substrates. These amine tracers may also be sulfonated to help make them water soluble. The non-halogenated tracers are introduced into the subterranean location in a form including, but not necessarily limited to, neat, encapsulated within a coating material that is inert with respect to the tracer, in an oil internal phase in an oil-in-water emulsion, in situ generation, and combinations thereof. The method additionally comprises recovering a fluid from the subterranean location where the fluid comprises the at least one non-halogenated tracer, where a majority of the plurality of the substrates remains within the subterranean location. The method further involves reacting the at least one non-halogenated tracer, optionally in a laboratory, with a reagent to give at least one derivatized tracer.

In another non-restrictive embodiment, there is provided a method for determining the presence of a tracer from a subterranean location that involves introducing at least one non-halogenated tracer into a subterranean location, where the at least one non-halogenated tracer is selected from the group consisting of primary or secondary alkyl and aromatic amines with the formula $H_2N$—R or R'—HN—R" having from 8 to 18 carbon atoms and salts of these amines, alkyl or aromatic diols having the formula HO—$(CH_2)_n$—OH, diamines having the formula $H_2N$—$(CH_2)_n$—$NH_2$, dicarboxylic acids having the formula HO.CO—$(CH_2)_n$—CO.OH, diesters having the formula R'O.CO—$(CH_2)_n$—CO.OR", where n is 4 to 18, and R' and R" are independently straight or branched alkyl or aromatic groups of 1-20 carbon atoms, and combinations thereof, where the non-halogenated tracer is absorbed into and/or adsorbed onto a plurality of substrates, where the non-halogenated tracer is introduced in a form including, but not necessarily limited to, neat, encapsulated within a coating material that is inert with respect to the tracer, in an oil internal phase in an oil-in-water emulsion, in situ generation, and combinations thereof. The method further involves recovering a fluid from the subterranean location where the fluid comprises the at least one non-halogenated tracer, where the fluid is selected from the group consisting of oil, water and combinations thereof, and reacting the at least one non-halogenated tracer with a reagent to give at least one derivatized tracer, where the reagent is one that can attach at least one halogen atom to the non-halogenated tracer. The method also includes detecting the at least one derivatized tracer from at least a portion of the recovered fluid.

In another non-limiting embodiment there may be provided a method for determining the presence of a tracer from a subterranean location that includes introducing at least one non-halogenated tracer into a subterranean location, where the at least one non-halogenated tracer is selected from the group consisting of primary or secondary alkyl and aromatic amines with the formula $H_2N$—R or R'—HN—R" having from 8 to 18 carbon atoms and salts of these amines, alkyl or aromatic diols having the formula HO—$(CH_2)_n$—OH, diamines having the formula $H_2N$—$(CH_2)_n$—$NH_2$, dicarboxylic acids having the formula HO.CO—$(CH_2)_n$—CO.OH, diesters having the formula R'O.CO—$(CH_2)_n$—CO.OR", where n is 4 to 18, and R' and R" are independently straight or branched alkyl or aromatic groups of 1-20 carbon atoms, and combinations thereof, where the non-halogenated tracer is absorbed into and/or adsorbed onto a plurality of substrates, where the non-halogenated tracer is introduced in a form selected from the group consisting of: neat, encapsulated within a coating material that is inert with respect to the tracer, in an oil internal phase in an oil-in-water emulsion, in situ generation, and combinations thereof. The method further involves recovering a fluid from the subterranean location where the fluid comprises the at least one non-halogenated tracer, where the fluid is selected from the group consisting of oil, water and combinations thereof, and where the amount of at least one derivatized tracer in the at least a portion of the recovered fluid is 0.02 mg/L or more. Additionally the method involves reacting the at least one non-halogenated tracer with a reagent to give at least one derivatized tracer, where the reagent includes, but is not necessarily limited to, pentafluoro benzyl chloride, pentafluoro benzoyl bromide, pentafluoro phenyl hydrazine, trifluoro acetic anhydride, trichloro ethanol, fluorophenyl silyl derivatives, and combinations thereof. The method further involves detecting the at least one derivatized tracer from at least a portion of the recovered fluid using a method selected from the group consisting of a gas chromatograph and an electron capture detector, a gas chromatograph with a mass spectrometer, high performance liquid chromatography with a mass spectrometer, and combinations thereof.

DETAILED DESCRIPTION

It has been discovered that a tracer detection method may be implemented using non-halogenated alkyl and/or aromatic amines, salts of these amines, diamines, diols, dicarboxylic acids, diesters, and combinations thereof as tracers and halogenated derivatives of the non-halogenated molecules in a laboratory for easy detection and separation. Advantages of the method described herein include that the non-halogenated tracers are relatively inexpensive and are readily available. They are also easily separated with a gas chromatograph equipped with an electron capture detector (ECD) and detected at very low levels. However, it will be appreciated that the method is not limited to GC/ECD; any other suitable technique may be used. The method described herein may also be performed with more expensive equipment such as a gas chromatograph with a mass spectrometer (GC/MS) in selective ion monitoring mode (SIM) or in negative chemical ionization mode. The method herein may also be practiced using a high performance liquid chromatograph with a mass spectrometer (HPLC/MS) with negative electro spray. There are likely other methods of detection; however GC/ECD is expected to be one of the most economical.

More specifically, the method herein involves the analysis of amines and salts thereof, diamines, diols, dicarboxylic acids and/or diesters as their derivatives to measure oil and/or water returns in produced wells, such as from a hydraulic fracturing operation. These amines and salts thereof, may be aliphatic, aromatic, saturated, unsaturated, and/or combinations thereof, and may have from 6 independently to 20 carbon atoms; alternatively from 8 independently to 18 carbon atoms. The diols may have the formula HO—$(CH_2)_n$—OH, the diamines may have the formula $H_2N$—$(CH_2)_n$—$NH_2$, the dicarboxylic acids may have the formula HO.CO—$(CH_2)_n$—CO.OH, and the diesters may have the formula R'O.CO—$(CH_2)_n$—CO.OR", where n is 6 to 16, and R' and R" are independently straight or branched alkyl or aromatic groups of 1-20 carbon atoms.

One suitable non-limiting example of a diol is 1,6-hexanediol. One suitable non-limiting example of a diamine is 1,6-hexanediamine. One suitable non-limiting example of a dicarboxylic acid is adipic acid. Suitable non-limiting examples of a diester are dialkyladipate esters, where the alkyl groups are independently straight or branched alkyl or aromatic groups of 1-20 carbon atoms.

The organic acid salts of these non-halogenated tracers are alkali metal or alkaline earth metal salts, including, but not necessarily limited to sodium, potassium and calcium salts of the organic acids, in a non-limiting instance the dicarboxylic acids. The salts of the acids are water soluble and can be extracted from the water to determine where the water comes from. Also possible to be used as tracers are sulfonated forms of these non-halogenated tracers as water soluble compounds. Suitable derivatives of these tracers may also be used.

The non-halogenated tracers may be introduced into one or more subterranean location in a variety of ways and/or using a number of different mechanisms used separately or together. In one non-limiting embodiment the tracers may be absorbed into and/or adsorbed onto a plurality of porous substrates. The tracers should remain absorbed into and/or adsorbed onto the substrate for a period of time sufficient for the substrate to be placed within a desired location, such as within a particular fracture complex, before the tracer begins to desorb from the substrate. That is, the tracer should not immediately desorb from the substrate, otherwise it will not function suitably as a tracer. It has been discovered that the non-halogenated tracers "stick" or remain absorbed into the substrates more readily than halogenated tracers, the latter which were found to quickly desorb. The amines and salts thereof, diamines, diols, dicarboxylic acids and/or diesters and sulfonated derivatives thereof behave more like hydrocarbons or water; and in particular the organic acid salts and amine salts behave more like water. Thus, the non-halogenated derivatives adhere or absorb into the substrates easily and are slow to desorb. In one non-limiting example, the tracer should remain substantially absorbed into the substrate within a time period of about 24 independently to about 250 hours; alternatively from about 24 independently to about 50 hours. Alternatively, the method may be understood as dependent on the volume of liquid produced from the formation and is not time dependent. In a non-limiting instance, it is desirable that the non-halogenated tracers recovered are detectable for at least 100 pore volumes of the induced fracture or more.

Suitable porous materials for the substrates include, but are not necessarily limited to, diatomaceous earth (DE), alumina, absorbent resinous materials or polymers, porous ceramic beads, walnut shell fragments, nut shells, silica particulate, precipitated silica, silica gel, activated carbon, zeolite, fullers earth, organic synthetic high molecular weight water-insoluble adsorbents molecular sieve, and combinations thereof. In one non-limiting embodiment, the substrate may be a proppant. Some of these water-insoluble absorbents are further described in U.S. Pat. Nos. 7,493,955 and 7,491,682, which are incorporated herein by reference in their entirety. It is well known that as a hydraulic fracturing fluid is pumped against and into the formation, the fluid may fracture the formation, thereby increasing its permeability and stimulating production. Proppants are used in the fluid to keep the fracture open after the procedure has been completed. As the fluid pressure is removed and the formation relaxes, the proppants keep the fracture open and increase permeability. The proppants and other porous media, such as the substrates, are thus disposed within and remain in fractures (or other subterranean structure). To summarize, the substrates may be different from, or the same as, the proppant used.

Proppants and substrates may have an average particle size of from about 125 independently to about 1700 microns. Common ranges for proppant average particle sizes in methods including frac packing and gravel packing include, but are not necessarily limited to, 12/18 mesh (about 1680 independently to about 1000 microns); 20/40 mesh (about 841 independently to about 400 microns); 30/50 mesh (about 595 independently to about 297 microns); 40/70 mesh (about 400 independently to about 210 microns); 100 mesh (149 microns) and in some instances below about 100 mesh (149 microns) as needed for certain applications.

The substrates may be beads or spheres that will take more closure pressure (the pressure exerted by the formation on the fracture to close) than DE, but such beads would need to be coated with a material, such as an outer shell, that slowly dissolves with time and temperature, thereby allowing the non-halogenated tracer to desorb slowly. Such suitable coatings or shell materials include, but are not necessarily limited to, polyvinylidene chlorides. The rate of desorption may be controlled by the nature of the coating or shell, the thickness of the coating or shell, and the fluids that will contact the coating or shell to dissolve it so that the tracer may be desorbed.

In another non-limiting embodiment, the non-halogenated tracer may be encapsulated whether or not it is absorbed into and/or adsorbed onto a substrate. That is, the tracer may be encapsulated in neat form. The coating material of the capsule shell may be a coating material that is inert with respect to the tracer. Optionally, the coating material may be an oil-soluble coating (hydrophobic), which dissolves in the crude oil of the formation or other hydrocarbon. Alternatively, controlled release of the tracers to the fluid phase may be designed using waxes as the coating materials which melt at certain bottom hole temperatures, such as in excess of 40° C., alternatively in excess of 100° C.

Suitable specific coating materials include, but are not necessarily limited to, polyvinylidene dichloride, polyethylene-co-polymethacrylates, ethylene vinyl acetate copolymers, polyamides, crosslinked ethylene copolymers, cellulosic materials, suitable water based polymers, and combinations thereof. Of the polyamides, nylon is one that is suitable, including, but not necessarily limited to nylon 6, 9, 12, 66 and mixtures thereof. Water soluble coatings that slowly dissolve in water, such as polyvinyl alcohol (PVA), and other water soluble coatings, are also expected to be suitable. With respect to cellulosic materials, ethylcellulose and methylcellulose are suitable. The coating material may be present in the encapsulated tracer an amount ranging from about 10 independently to about 90 wt % and the non-halogenated tracer may be present in the encapsulated tracer an amount ranging from about 90 independently to about 10 wt %; alternatively, the encapsulated tracer may be present in an amount from about 20 independently to about 40 wt %; where the coating material ranges from about 80 independently to about 60 wt %.

The size of the encapsulated tracers may be the exterior sizes for the substrates and the proppants noted previously. The thickness of the coating of the encapsulated tracers may be designed to time the release of the tracers into the fluid phase, where a thinner shell provides for quicker release and a thicker shell provides for a more delayed release. In one non-limiting embodiment the coating material or shell thickness may be from about 5 to about 25 microns thick.

Methods that may be used to encapsulate or microencapsulate the tracers are known in the art, such as those described in U.S. Pat. No. 5,164,099 directed to encapsulation for treating subterranean formations, as well as U.S. Pat. Nos. 6,126, 872; 6,160,036; and 6,841,593; all of which are incorporated herein by reference in their entirety.

In another non-limiting embodiment, the non-halogenated tracer may be introduced downhole as part of an emulsion, in a non-limiting instance in an oil internal phase in an oil-in-water emulsion. When the emulsion is broken, for instance through a mechanism including, but not necessarily limited to, elevated temperature, dilution, agitation (such as the shear forces involved in injecting the carrier fluid into a fracture), or combinations of these, then the tracer is delivered to the surrounding fluid. In another non-restrictive version, the tracer is present in an oil internal phase in an oil-in-water emulsion stabilized by an effective stabilizing amount of an emulsifying agent having a hydrophilic-lipophilic balance (HLB) between about 4 independently to about 20. An alternative HLB range is from about 8 independently to about 12. In a non-limiting embodiment the amount of non-halogenated tracer in the emulsion may range between about 1 independently to about 95 wt %; alternatively from about 2 independently to about 10 wt %; and the balance being aqueous and hydrocarbon phases where the amount of emulsifying agent ranges from about 1 independently to about 100 gallon per thousand gallons (about 1 liter per thousand liters or other convenient SI unit), alternatively from about 2 independently to about 10 gpt, based on the total oil-in-water emulsion. In the case of water-soluble non-halogenated tracer, the water-soluble non-halogenated tracer would be in or be an internal discontinuous aqueous phase within an oil external phase; namely be a water-in-oil emulsion.

Suitable emulsifying agents include, but are not necessarily limited to, sorbitol oleates, polyalkyl ether alcohol ethers, and/or their sulfates, and the like. A suitable aspect of this delivery mechanism involves adding the emulsified non-halogenated tracer compounds to the fracturing fluid at a suitable dosage and pumping the chemicals downhole.

The particle sizes of the internal oil phase droplets may range from about 10 independently to about 500 microns; alternatively from about 50 independently to about 200 microns.

In another non-limiting embodiment, the non-halogenated tracer may be used neat; that is, without using a substrate, encapsulation or an emulsion. In this embodiment, the dosages of the non-halogenated tracer in a carrier fluid may range from about 0.01% independently to about 10% wt %, alternatively from about 0.05% independently to about 3.0 wt %. The carrier fluid may be oil, water or a combination thereof.

In still another non-limiting embodiment, the non-halogenated tracer may be generated in situ. By "in situ" is meant in place in any subterranean location including, but not necessary limited to, a wellbore, a subterranean formation, a fracture, and the like and combinations thereof. In one non-restrictive version, the non-halogenated tracer is generated in situ by hydrolysis from a compound selected from group consisting of the corresponding ester, the corresponding amide, the corresponding anhydride, the corresponding cyclic ester (lactone), and combinations thereof. Such hydrolysis can often be aided by addition of about 1 to 2 equivalents of a base (including, but not necessarily limited to NaOH, KOH, $K_2CO_3$ and the like) that catalyzes the hydrolysis of these compounds with water present. The esters hydrolyze in this way to their parent acids and alcohols, both non-halogenated tracers described in the methods herein. The amides/cyclic esters hydrolyze in this fashion to their acid derivatives. In a specific example, cetyl palmitate is $C_{16}CO_2C_{16}$; when hydrolyzed in the presence of base this product yields $C_{16}$—OH and $C_{15}CO_2H$; similar compounds can be generically described as $R^1$—$CO_2$—$R^2$ (the esters of formula (1)); where $R^1$ and $R^2$ are independently C10-C30 linear or branched alkyl or aromatic compounds. Amines suitable as non-halogenated tracers may be formed from the hydrolysis of amides (O=C—$NH_2$). The in situ non-halogenated tracer may also be acid catalyzed, such as by using a mineral acid and/or an organic acid. Specific suitable acids include, but are not necessarily limited to, HCl, HBr, $HNO_3$ and the like, or acetic acid, citric acid and the like. Again, about 1 mole of ester/amide is used with about 1 to 2 equivalents of base or acid. The hydrolysis reaction is facilitated by the higher temperatures encountered in reservoir conditions.

The addition of a strong base will convert the organic acids to acid salts which make them water soluble. A strong base is defined as any material having the ability to create a pH in water of 9.0 or above. Heat also will also degrade esters to the acids and alcohols. Heat is defined as a temperature in the range between about 150 to about 250° C. In addition oxidizers, such as permanganates and peroxides, will do the same thing. The addition of strong acids will convert amines to amine salts, which are water soluble. A strong acid is defined as any material which has a pH of less than 5.0

Suitable derivatizing reagents to react with the non-halogenated tracers include, but are not necessarily limited to, any reagent that can attach at least one halogen atom to the non-halogenated tracer. Non-limiting examples include, but are not necessarily limited to, pentafluoro benzyl chloride, pentafluoro benzoyl bromide, pentafluoro phenyl hydrazine, trifluoroacetic anhydride, and 2,2,2,trichloroethanol to make sensitive derivatives of compounds that may be used to determine the presence of these com-pounds by gas chromatography with an electron capture detector (GC/ECD). To be explicit, one type of derivatizing reagent within this definition is fluorophenyl silyl derivatives, such as flophemesyl amine, which may react with alcohols, such as in the following reaction.

While the use of these derivatized tracers has been known, it has not been re-invented or applied to the production of hydrocarbons until now. These compounds are known in other industries such as medicine or the environmental industry to measure these items at extremely low levels in other materials, but not used as tracers. It is surprising and unexpected to use these tracers in oilfield produced water and/or oil, without the use of halogenated tracer compounds to begin with. The method herein uses non-halogenated or halogen-free amines, alcohols, ketones, and/or organic acids. The use of these non-halogenated molecules saves a large expense because the halogenated compounds are far more expensive (by orders of magnitude) than the corresponding non-halogenated amines, alcohols, ketones and/or organic acids.

Fluorinated benzoic acid has been used in the past as a tracer, where benzoic acid has been fluorinated prior to use. An important distinction in the present method is that none of the compounds are fluorinated (or otherwise halogenated) until they come back to the surface and are transported to a laboratory (stationary or mobile) for derivatization (reaction with a derivatizing agent such as pentafluoro benzyl chloride) and detection. While non-fluorinated benzoic acid or alkyl aromatic acids may be used in the present method, if fluorinated derivatives were made of those compounds, they would not be the same derivatives as those used in the prior methods; they would be, e.g., a fluorinated ester of the benzoic acid (two aromatic rings connected by an ether linkage where one is fluorinated and the other is not).

One embodiment of a method of using the tracers as described herein is that the non-halogenated tracers would be applied at a rate of about 10 lbs per barrel (about 27 grams/liter) of a single tracer absorbed on a substrate, such as SORB™ or MULTISORB™ scale inhibitors available from Baker Hughes, into a single frac stage and then look for it to be produced back. Every frac stage may have a different identifiable compound in it or perhaps two tracer compounds; one that is oil soluble and one that is water soluble. Then, when the well is put back online, a sample of the water and oil is sent to the laboratory for analysis. In the lab the sample is derivatized so that the compound may be detected at the lowest detection level. The tracers may be derivatized with pentafluoro benzyl chloride or similar reagents to form the pentafluoro amide, ether, ester or hydrazine of the tracer compound for detection and analysis by gas chromatography with an electron capture detector. The acids may also be derivatized with reagents, such as trichloro ethanol, to make trichloro ethyl esters. Trifluoro acetic anhydride may be used to make trifluoro amide derivatives of the amines. Other suitable derivatizing agents include, but are not necessarily limited to, pentafluoro benzoyl bromide, pentafluoro phenyl hydrazine and the like. Details about derivatizing the non-halogenated tracers may be found in Daniel P. Knapp, *Handbook of Analytical Derivatization Reactions*, John Wiley and Sons, 1979, and Karl Blau and John Halket, *Handbook of Derivatives for Chromatography*, John Wiley and Sons 1993, both of which are incorporated by reference herein in their entirety. It should be emphasized that the derivatized tracers for chromatography in the method described herein are not halogenated compounds to begin with. As a matter of fact, most of the derivatives discussed in both books have nothing to do with halogens. These references primarily describe methods to derivatize compounds for GC or HPLC analysis that are difficult to analyze by chromatography by themselves.

From this procedure it may be determined which frac stage is producing the water and which frac stage is producing the oil. A broad detection range would be a detection of hundreds of mg/L of the compounds to as low as about 0.02 mg/L of the tracers. The detection level would be dependent on the amount of produced water and the total flow rates of oil and water from the well.

The chemical reaction schemes shown below describe these derivatization reactions, for example, in the case of an aliphatic amine (I), an aliphatic diamine (II), an aliphatic diol (III) and an aliphatic dicarboxylic acid (IV) where n=7-27. The derivatives may be formed as follows, N-trifluoroacetyl amines (V), bis-N,N'-trifluoroacetylamines (VI), bis-aliphatic alcohol esters of pentafluorobenzoic acid (VII), bis-pentafluorobenzylester of the aliphatic dicarboxylic acid (VIII) and the bis-trichloroethyl ester of the aliphatic dicarboxylic acid (IX)

-continued (VIII)

(IV)
(n = 7 to 27)

(IX)

The invention will now be described with respect to particular embodiments of the invention which are not intended to limit the invention in any way, but which are simply to further highlight or illustrate the invention.

EXPERIMENTAL

Figure 3:
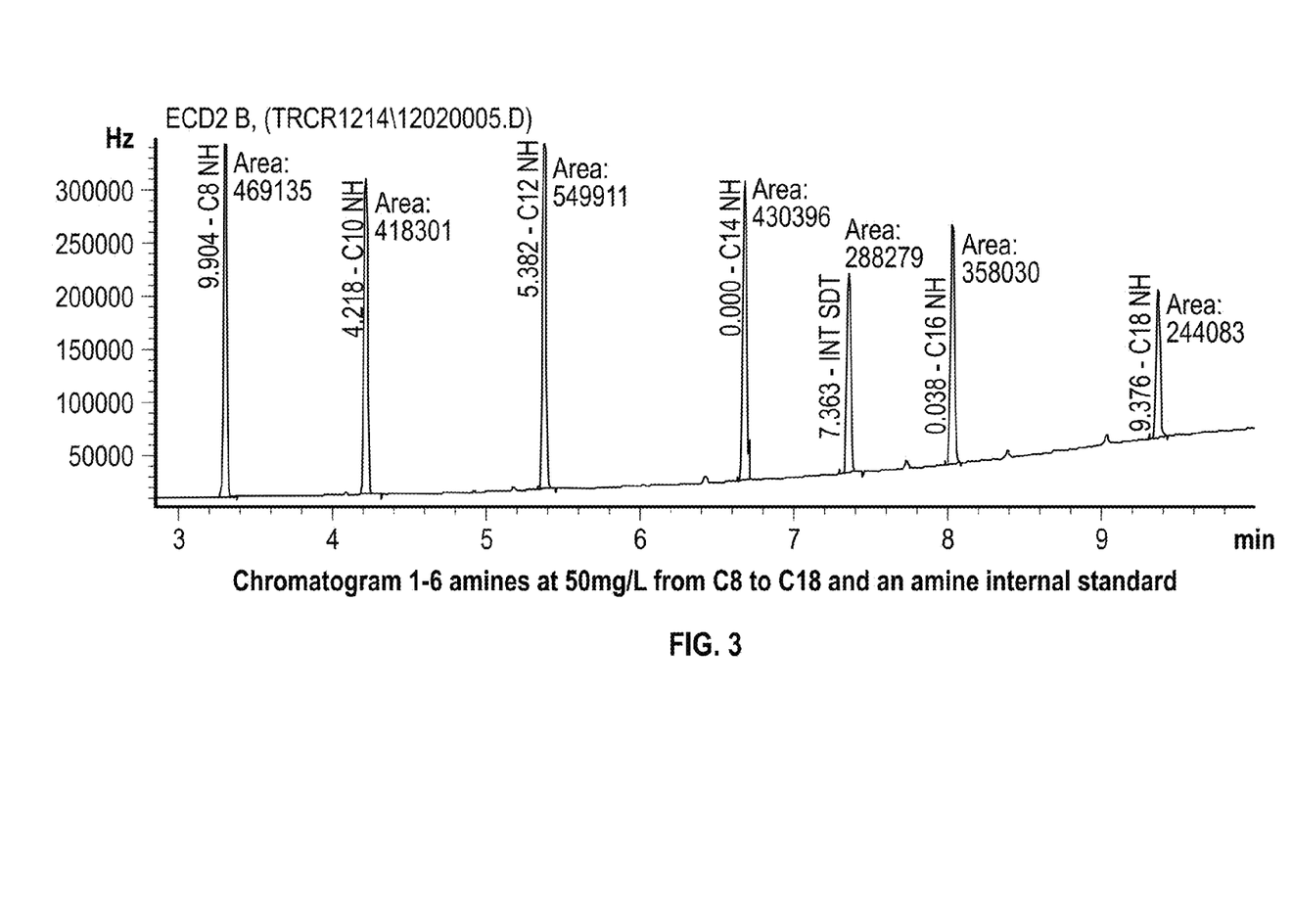
FIG. 3 (Chromatogram 1) is a chromatogram of six amines at 50 mg/L plus an internal standard showing that it is almost off scale at this concentration.

The following aliphatic primary amine salts have been tested from 100 mg/L to 5 mg/L C8, C10, C12, C14, C15 (used as an internal standard), C16, and C18. To a 1 mL sample of the amine salts in water a drop of 50% NaOH was added as well as a measured amount of the internal standard (C15) and a few mL of hexane. The sample was vigorously shaken for 30 seconds and the amines salts were thereby converted to the amines and extracted into the hexane. The hexane phase was then derivatized for analysis by GC/ECD using an appropriate reagent. See Chromatogram 1 (FIG. 3). It is thus expected that any alcohols, ketones, organic acids and their salts, amines and salts thereof, diamines, diols, dicarboxylic acids and/or diesters will work regardless of whether they are aliphatic straight chains, branched chains, whether they contain unsaturation or even have aromatic rings or saturated rings structures.

While one concern is that there may be naturally occurring compounds present in crude oils that would interfere with the analysis of the tracers, three different blank crudes have been analyzed using derivatized tracers and it has been determined that none of them would have interfered with the analysis.

Figure 4:
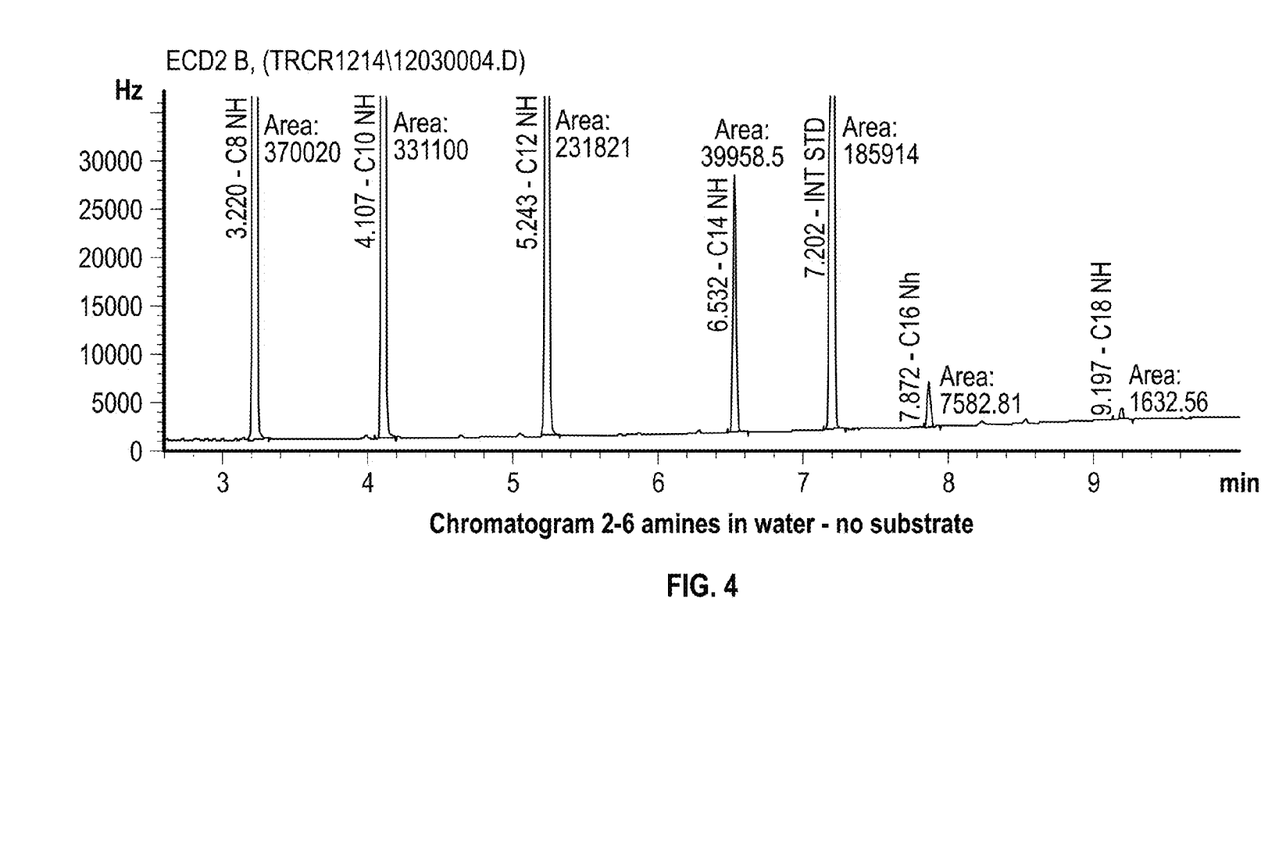
FIG. 4 (Chromatogram 2) is the same concentration as the amine salt, converted back to the amine and reacted as Chromatogram 1.

The difference in analytical results of the chromatograms between a blank crude and a sample containing the derivatized alcohol tracers is dramatic. A water sample with a C15 amine added may be used as an internal standard. Internal standards are used to show that the response in water is essentially the same as the standard. The chromatogram is a relatively smooth curve with a spike for the C15 amine. A chromatogram of a sample with seven amines from C10 to C18 and the same C15 internal standard shows a noticeable peak for each amine in the relatively smooth curve giving a very remarkable contrast. The chromatogram of the amine standard showing that the C15 internal standard at 41.5 mg/L has a peak height of 220,000 Hz while the same internal standard extracted from a water sample has a peak height of 300,000 Hz. Thus, if derivatized amines were in the water, they would be seen. See Chromatogram 2 (FIG. 4).

Tracer Returns Study

Figure 1:
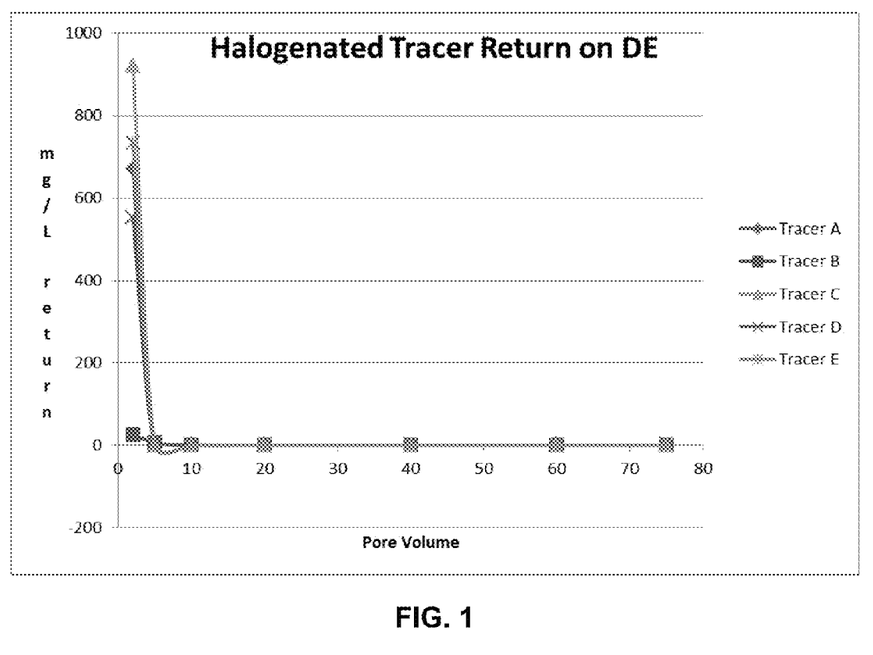
FIG. 1 is a graph of the returns of a 2% solution of five commercially-available halogenated tracers from a U.S. tracer supplier on diatomaceous earth (DE) demonstrating that the halogenated tracers come off the DE immediately.

Shown in FIG. 1 is a graph of the returns of a 2% solution of 5 commercially available halogenated tracers from a U.S. tracer supplier on diatomaceous earth (DE). The samples were put onto the DE and then washed off with successive column volumes of ISOPAR "L". ISOPAR "L" is a pure alkyl hydrocarbon used to simulate crude oil in the laboratory. What is seen is that the halogenated tracers come off the DE right away and go to zero detection almost immediately. Thus, from a field detection standpoint, if one does not catch the sample right away, it will be lost. In fact, it is readily seen that Tracer B came back so quickly, it was almost not found.

Figure 2:
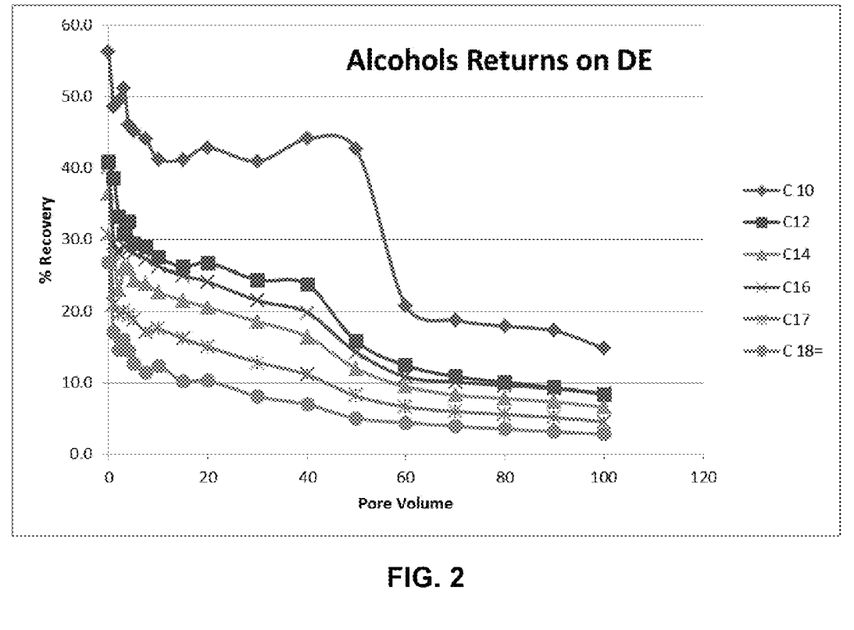
FIG. 2 shows data for alcohol returns generated from a 1% loading of alcohols on diatomaceous earth (half as much loading as for FIG. 1)

In contrast to the FIG. 1 data, the FIG. 2 graph shows data generated from a 1% loading of alcohols on DE (half as much loading as for FIG. 1). The sample was washed with the same ISOPAR to simulate crude oil and the alcohol(s) content was measured in the return fluids with pore volume returns. What was seen was that the alcohols came off the DE much more slowly and in a more predictable manner for a longer period of time than the halogenated tracers of FIG. 1. This allows for a longer testing period and more useful data.

It should be noted that the Y axis for the two graphs of FIGS. 1 and 2 are slightly different. The Y axis for FIG. 1 is mg/L and the Y axis for FIG. 2 is as a % of the sample put on the DE. This is because the amount of each alcohol put on the column was slightly different and the experimenters wanted to compare them to each other for return properties. Actual returns were from a 60 mg/L to 30 mg/L for the first pore volumes to a low of 16.8 mg/L to 2.8 mg/L at 100 pore volumes for FIG. 2. If FIG. 1 was compared in the same way, the first sample point would be at 10% and go to zero by the second sample point. The real problem is that the halogenated tracers do not "stick" or absorb into and/or adsorb onto the DE to begin with. In contrast, the alcohols, acids, ketones, amines and salts thereof, diamines, diols, dicarboxylic acids and/or diesters of the method described herein will "stick" (absorb into and/or adsorb onto) to the DE and come off of it slower.

It is to be understood that the invention is not limited to the exact details of procedures, operation, exact materials, or embodiments shown and described, as modifications and equivalents will be apparent to one skilled in the art. Accordingly, the invention is therefore to be limited only by the spirit and scope of the appended claims. Further, the specification is to be regarded in an illustrative rather than a restrictive sense. For example, specific combinations of non-halogenated tracers, amines and salts thereof, diamines, diols, dicarboxylic acids and/or diesters, sulfonated tracers, derivatizing agents, substrates, derivatized agents, fracturing stages used, derivatizing reaction conditions, coating materials, emulsifying agents, but not specifically identified or tried in a particular method, are anticipated to be within the scope of this invention.

The terms "comprises" and "comprising" in the claims should be interpreted to mean including, but not limited to, the recited elements.

The present invention may suitably comprise, consist of or consist essentially of the elements disclosed and may be practiced in the absence of an element not disclosed. For instance, there may be provided a method for determining the presence of a derivatized tracer from a subterranean location that consists essentially of or consists of introducing at least one non-halogenated tracer into a subterranean location, where the at least one non-halogenated tracer is selected from the group consisting of primary or secondary alkyl and aromatic amines with the formula $H_2N$—R or R'—HN—R" having from 8 to 18 carbon atoms and salts of these amines, alkyl or aromatic diols having the formula HO—$(CH_2)_n$—OH, diamines having the formula $H_2N$—$(CH_2)_n$—$NH_2$, dicarboxylic acids having the formula HO.CO—$(CH_2)_n$—CO.OH, diesters having the formula R'O.CO—$(CH_2)_n$—CO.OR", where n is 4 to 18, and R' and R" are independently straight or branched alkyl or aromatic groups of 1-20 carbon atoms, and combinations thereof, where the non-halogenated tracer is absorbed into and/or adsorbed onto a plurality of substrates; where the non-halogenated tracer is introduced in a form selected from the group consisting of neat, encapsulated within a coating material that is inert with respect to the tracer, in an oil internal phase in an oil-in-water emulsion, in situ generation, and combinations thereof; recovering a fluid from the subterranean location where the fluid comprises the at least one non-halogenated tracer; reacting the at least one non-halogenated tracer with a reagent to give at least one derivatized tracer; and optionally detecting the at least one derivatized tracer from at least a portion of the recovered fluid.

What is claimed is:

1. A method for determining a presence of a tracer from a subterranean location comprising:
   introducing at least one non-halogenated tracer into a subterranean location, where the at least one non-halogenated tracer is selected from the group consisting of primary or secondary alkyl and aromatic amines with the formula $H_2N$—R or R'—HN—R" having from 8 to 18 carbon atoms and salts of these amines, alkyl or aromatic diols having the formula HO—$(CH_2)_n$—OH, diamines having the formula $H_2N$—$(CH_2)_n$—$NH_2$, dicarboxylic acids having the formula HO.CO—$(CH_2)_n$—CO.OH, diesters having the formula R'O.CO—$(CH_2)_n$—CO.OR", where n is 4 to 18, and R' and R" are independently straight or branched alkyl or aromatic groups of 1-20 carbon atoms, and combinations thereof, where the non-halogenated tracer is absorbed into and/or adsorbed onto a plurality of substrates;
   recovering a fluid from the subterranean location where the fluid comprises the at least one non-halogenated tracer; and
   reacting the at least one non-halogenated tracer with a reagent to give at least one derivatized tracer, where the reagent is a reagent that can attach at least one halogen atom to the non-halogenated tracer.

2. The method of claim 1 where the non-halogenated tracer is introduced in a form selected from the group consisting of:
   neat,
   encapsulated within a coating material that is inert with respect to the tracer,
   in an oil internal phase in an oil-in-water emulsion, and
   in situ generation.

3. The method of claim 1 where the reagent is selected from the group consisting of pentafluoro benzyl chloride, pentafluoro benzoyl bromide, pentafluoro phenyl hydrazine, trifluoro acetic anhydride, trichloro ethanol, fluorophenyl silyl derivatives, and combinations thereof.

4. The method of claim 1 where the amount of at least one derivatized tracer in the at least a portion of the recovered fluid is 0.02 mg/L or more.

5. The method of claim 1 where the fluid is selected from the group consisting of oil, water and combinations thereof.

6. The method of claim 1 where:
   the introducing comprises:
      introducing a first non-halogenated tracer into a first subterranean location in a first fracturing stage;
      introducing a second non-halogenated tracer into a second subterranean location in a second fracturing stage different from the first stage;
   recovering a first fluid containing the first non-halogenated tracer from the first subterranean location and recovering a second fluid containing the second non-halogenated tracer from the second subterranean location; and
   the reacting comprises:
      reacting the first non-halogenated tracer with a reagent to give a first derivatized tracer, where the reagent is a reagent that can attach at least one halogen atom to the non-halogenated tracer, and
      reacting the second non-halogenated tracer with a reagent to give a second derivatized tracer different from the first derivatized tracer, where the reagent is a reagent that can attach at least one halogen atom to the non-halogenated tracer;
   detecting and distinguishing the fluid containing the first derivatized tracer and the fluid containing the second derivatized tracer.

7. The method of claim 1 where the tracer is encapsulated within a coating material and the coating material is selected from the group consisting of polyvinylidene dichloride, polyethylene-co-polymethacrylates, ethylene vinyl actetate copolymers, polyamides, crosslinked ethylene copolymers, cellulosic materials, and combinations thereof.

8. The method of claim 1 where the tracer is encapsulated within a coating material, and the coating material is present in the encapsulated tracer an amount ranging from about 10 to about 90 wt % and the non-halogenated tracer is present in the encapsulated tracer an amount ranging from about 90 to about 10 wt %.

9. The method of claim 1 where tracer is present in an oil internal phase in an oil-in-water emulsion stabilized by an effective stabilizing amount of an emulsifying agent having an hydrophilic-lipophilic balance between about 8 and about 20.

10. The method of claim 9 where the amount of non-halogenated tracer ranges between about 10 to about 95 wt % and the balance being aqueous and hydrocarbon phases where the amount of emulsifying agent ranges from about 1 to about 100 gallon per thousand gallons (about 1 liter per thousand liters), based on the total oil-in-water emulsion.

11. The method of claim 1 where the non-halogenated tracer is generated in situ in the subterranean formation by hydrolysis from a compound selected from group consisting of the corresponding ester, the corresponding amide, the corresponding anhydride, the corresponding cyclic ester (lactone), and combinations thereof.

12. A method for determining a presence of a tracer from a subterranean location comprising:
   introducing at least one non-halogenated tracer into a subterranean location, where the at least one non-halogenated tracer is selected from the group consisting of primary or secondary alkyl and aromatic amines with the formula $H_2N$—R or R'—HN—R" having from 8 to 18 carbon atoms and salts of these amines, alkyl or aromatic diols having the formula HO—$(CH_2)_n$—OH, diamines having the formula $H_2N$—$(CH_2)_n$—$NH_2$, dicarboxylic acids having the formula HO.CO—$(CH_2)_n$—CO.OH, diesters having the formula R'O.CO—$(CH_2)_n$—CO.OR", where n is 4 to 18, and R' and R" are independently straight or branched alkyl or aromatic groups of 1-20 carbon atoms, and combinations thereof, where the non-halogenated tracer is absorbed into and/or adsorbed onto a plurality of substrates;

recovering a fluid from the subterranean location where the fluid comprises the at least one non-halogenated tracer, where the fluid is selected from the group consisting of oil, water and combinations thereof;

reacting the at least one non-halogenated tracer with a reagent to give at least one derivatized tracer, where the reagent is one that can attach at least one halogen atom to the non-halogenated tracer;

detecting the at least one derivatized tracer from at least a portion of the recovered fluid.

13. The method of claim 12 where the reagent is selected from the group consisting of pentafluoro benzyl chloride, pentafluoro benzoyl bromide, pentafluoro phenyl hydrazine, trifluoro acetic anhydride, trichloro ethanol, fluorophenyl silyl derivatives, and combinations thereof.

14. The method of claim 12 where the amount of at least one derivatized tracer in the at least a portion of the recovered fluid is 0.02 mg/L or more.

15. The method of claim 12 further comprising detecting the at least one derivatized tracer using a method selected from the group consisting of a gas chromatograph with an electron capture detector, a gas chromatograph with a mass spectrometer, high performance liquid chromatography with a mass spectrometer, and combinations thereof.

16. The method of claim 12 where:
the introducing comprises:
introducing a first non-halogenated tracer into a first subterranean location in a first fracturing stage;
introducing a second non-halogenated tracer into a second subterranean location in a second fracturing stage different from the first stage;
recovering a first fluid containing the first non-halogenated tracer from the first subterranean location and recovering a second fluid containing the second non-halogenated tracer from the second subterranean location;
the reacting comprises:
reacting the first non-halogenated tracer with a reagent to give a first derivatized tracer, where the reagent is a reagent that can attach at least one halogen atom to the non-halogenated tracer, and
reacting the second non-halogenated tracer with a reagent to give a second derivatized tracer different from the first derivatized tracer, where the reagent is a reagent that can attach at least one halogen atom to the non-halogenated tracer;
detecting and distinguishing the fluid containing the first derivatized tracer and the fluid containing the second derivatized tracer.

17. A method for determining a presence of a tracer from a subterranean location comprising:
introducing at least one non-halogenated tracer into a subterranean location, where the at least one non-halogenated tracer is selected from the group consisting of primary or secondary alkyl and aromatic amines with the formula $H_2N-R$ or $R'-HN-R''$ having from 8 to 18 carbon atoms and salts of these amines, alkyl or aromatic diols having the formula $HO-(CH_2)_n-OH$, diamines having the formula $H_2N-(CH_2)_n-NH_2$, dicarboxylic acids having the formula $HO.CO-(CH_2)_n-CO.OH$, diesters having the formula $R'O.CO-(CH_2)_n-CO.OR''$, where n is 4 to 18, and R' and R'' are independently straight or branched alkyl or aromatic groups of 1-20 carbon atoms, and combinations thereof, where the non-halogenated tracer is absorbed into and/or adsorbed onto a plurality of substrates;

recovering a fluid from the subterranean location where the fluid comprises the at least one non-halogenated tracer, where the fluid is selected from the group consisting of oil, water and combinations thereof, where the amount of at least one derivatized tracer in the at least a portion of the recovered fluid is 0.02 mg/L or more;

reacting the at least one non-halogenated tracer with a reagent to give at least one derivatized tracer, where the reagent is selected from the group consisting of pentafluoro benzyl chloride, pentafluoro benzoyl bromide, pentafluoro phenyl hydrazine, trifluoro acetic anhydride, trichloro ethanol, and combinations thereof; and detecting the at least one derivatized tracer from at least a portion of the recovered fluid using a method selected from the group consisting of a gas chromatograph and an electron capture detector, a gas chromatograph with a mass spectrometer, high performance liquid chromatography with a mass spectrometer, and combinations thereof.

18. The method of claim 17 where:
the introducing comprises:
introducing a first non-halogenated tracer into a first subterranean location in a first fracturing stage;
introducing a second non-halogenated tracer into a second subterranean location in a second fracturing stage different from the first stage;
recovering a first fluid containing the first non-halogenated tracer from the first subterranean location and recovering a second fluid containing the second non-halogenated tracer from the second subterranean location; and
the reacting comprises:
reacting the first non-halogenated tracer with a reagent to give a first derivatized tracer and
reacting the second non-halogenated tracer with a reagent to give a second derivatized tracer different from the first derivatized tracer;
detecting and distinguishing the fluid containing the first derivatized tracer and the fluid containing the second derivatized tracer.

19. The method of claim 17 where the non-halogenated tracer is introduced in a form selected from the group consisting of:
neat,
encapsulated within a coating material that is inert with respect to the tracer,
in an oil internal phase in an oil-in-water emulsion, and
in situ generation.

\* \* \* \* \*